(12) United States Patent
Aceti

(10) Patent No.: US 6,253,871 B1
(45) Date of Patent: Jul. 3, 2001

(54) DISPOSABLE IN-THE-EAR MONITORING INSTRUMENT USING A FLEXIBLE EARMOLD AND CASING, AND METHOD OF MANUFACTURE

(75) Inventor: John Gregory Aceti, Cranbury, NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 09/264,656

(22) Filed: Mar. 8, 1999

Related U.S. Application Data

(63) Continuation-in-part of application No. 08/850,670, filed on May 2, 1997, now Pat. No. 5,979,589, and a continuation-in-part of application No. 08/815,852, filed on Mar. 12, 1997, now Pat. No. 5,881,159.

(51) Int. Cl.$^7$ ............................................. A61B 7/02
(52) U.S. Cl. ........................ 181/135; 181/130; 381/328
(58) Field of Search ................................ 181/135, 134, 181/130, 129; 381/328, 322; 128/865, 867, 864

(56) References Cited

U.S. PATENT DOCUMENTS

| | | | | |
|---|---|---|---|---|
| 3,598,928 | * | 8/1971 | Hickox | 179/107 |
| 5,068,902 | * | 11/1991 | Ward | 381/68.6 |
| 5,606,621 | * | 2/1997 | Reiter et al. | 381/68.6 |
| 5,881,159 | * | 3/1999 | Aceti et al. | 381/328 |
| 5,887,070 | * | 3/1999 | Iseberg et al. | 381/380 |

* cited by examiner

*Primary Examiner*—Paul Ip
*Assistant Examiner*—Edgardo San Martin
(74) *Attorney, Agent, or Firm*—William J. Burke

(57) ABSTRACT

A disposable in-the-ear monitoring instrument includes a monitoring assembly for monitoring one or more vital health signs of a user, a transmitter assembly for transmitting the monitored vital health signs to a remote receiving unit, and a battery which is sealed within the monitoring instrument for energizing the assemblies. The assemblies and battery are mounted on a flexible printed circuit which is disposed in a flexible, cylindrical casing. And the casing itself is mounted in an earmold made of soft and compliant material, with conical fins extending from an outer surface of the earmold so that the earmold and monitoring circuitry may be easily deformed to comfortably fit a user. The disposable in-the-ear monitoring instrument is of a design having minimal components, and thus is easy to assemble on an automated basis. The automated assembly of the in-the-ear monitoring instrument and its minimal design reduces cost and allows for the disposability of the monitoring instrument.

32 Claims, 2 Drawing Sheets

DISPOSABLE IN-THE-EAR MONITORING INSTRUMENT USING A FLEXIBLE EARMOLD AND CASING, AND METHOD OF MANUFACTURE

This is a continuation-in-part of application Ser. No. 08/815,852 filed Mar. 12, 1997, now U.S. Pat. No. 5,881,159, Mar. 9, 1999 and of application Ser. No. 08/850,670 filed May 2, 1997, now U.S. Pat. No. 5,979,589, Nov. 9, 1999.

FIELD OF THE INVENTION

The present invention relates to an in-the-ear monitoring instrument and method of manufacture, and more particularly to a disposable in-the-ear monitoring instrument using a flexible earmold and casing which fits tightly and comfortably in ear canals of various sizes and shapes.

BACKGROUND OF THE INVENTION

The present invention involves an in-the-ear monitoring instrument having the form factor of a hearing aid. Most hearing aids include an earmold which is inserted and retained in the canal of the ear of the user. The earmold may contain the electronics of the hearing aid, including the receiver, or may be connected to the electronics, which are outside the canal of the ear, by a tube. The earmold desirably fits comfortably in the ear and is formed in a manner that it is readily retained in the canal of the ear. Retention of the earmold in the ear canal may be accomplished by friction and/or mechanical locking. Friction is created by radial pressure of the earmold on the wall of the canal. The more pressure, the greater is the retention force. However, friction is also dependent on lubricants between the earmold and the wall of the canal. The presence of cerumen (ear wax), perspiration or water significantly reduces friction retention. Therefore, mechanical locking is the primary means by which most hearing aids are retained in the ear. For mechanical locking, the earmolds are molded to fit the complex shape of the ear canal. These complex interlocking shapes hold the hearing aid in place without relying on friction so that they are not susceptible to the loosening caused by forces which tend to dislodge the hearing aid. However, the making of these complex interlocking shapes is a laborious, inaccurate and time consuming process which often requires the user to make several visits to the audiologist or dispenser before an earmold with a secure fit can be made. This is not only time consuming, but also greatly increases the cost of the hearing aid.

Two of the more recent attempts at commercializing preformed earmolds are shown in U.S. Pat. No. 4,870,688 to B. Voroba et al., issued Sep. 26, 1989, entitled MASS PRODUCTION AUDITORY CANAL HEARING AID, and U.S. Pat. No., 5,002,151 to R. J. Oliveira et al., issued Mar. 26, 1991, entitled EAR PIECE HAVING DISPOSABLE, COMPRESSIBLE POLYMERIC FOAM SLEEVE. The earmold shown in the patent to Oliveira et al. uses a compressible retard recovery foam that can be compressed and then inserted into a person's ear, and allowed to recover to fill into the canal. This earmold is held in only by friction. Also, the earmold is connected to the electronics by a tube which has the tendency to pull on the earmold frequently and thus dislodge it. For this reason, these devices are limited to short trial periods.

The hearing aid shown in the patent to Voroba et al. uses a soft polymeric material in solid form. The earmold is designed to utilize both friction and mechanical locking. However, the earmold contains the electronics and, so, the weight and cantilever of the hear aid tends to dislodge the earmold over time. To support the cantilever, the Voroba et al. earmold is designed to fill in the canal and the concha. However, making a generic earmold which fits well both in the canal and in the concha is difficult. Also, the earmold of Voroba et al. is designed for several years of use, requiring that is be made of a harder material.

The use of a generic earmold and casing could also have applications for an in-the-ear monitoring instrument.

Monitoring the vital health signs of a patient typically requires excessive time of medical personnel, or the patient being inconvenienced by being connected by wires to bulky monitoring equipment. For example, in a hospital setting, a nurse has to travel from patient-to-patient in order to determine such vital health signs as temperature and pulse. These account for a substantial amount of the nurse's time and do not provide continuous data. Continuously monitoring vital health signs may require the use of cumbersome and expensive equipment, and may cause the patient discomfort and inconvenience because this equipment has to be connected to the patient and thereby limiting the patient's mobility. Both the time expended by medical personnel in obtaining vital health signs of patients, as well as the bulky equipment required, can account for a substantial cost in caring for patients.

It would be desirable to have a simple low cost in-the-ear monitoring instrument which uses a generic earmold and casing that fits securely and comfortably in ear canals of various sizes and shapes. This monitoring instrument continuously or continually monitors a patient's vital health signs and transmits these vital health signs to a remote monitoring unit without the need for the patient being physically connected to the monitoring unit. It would also be most desirous if such monitoring instrument were relatively non-intrusive to the patient and if the monitoring instrument were relatively inexpensive with regard to both the structure of its components and its method of manufacture. In addition, it would be desirable for such a monitoring instrument to have an integral power source and to be so inexpensive that it could be disposed of after its power source expires.

SUMMARY OF THE INVENTION

The present invention is directed to a disposable in-the-ear monitoring instrument including an earmold and casing. The earmold and casing have one or more monitors for monitoring vital health signs of a user, a transmitter for receiving signals from the one or more monitors representative of monitored vital health signs and for transmitting such signals to a remote receiving unit where they can be read. A battery is permanently electrically connected to the monitor and transmitter and sealed in the monitoring instrument.

In a method for assembly of the disposable in-the-ear monitoring instrument, electrical components, monitoring components and batteries are connected to an elongated flexible printed circuit strip. The printed circuit strip provides a plurality of assemblies, and is cut apart to form individual assemblies each for a disposable in-the-ear monitoring instrument. Each assembly is placed in a flexible casing, and each casing is in-turn placed in an earmold of a soft, durable and compliant material with a plurality of fins projecting outwardly from the earmold.

BRIEF DESCRIPTION OF THE DRAWING

For a fuller understanding of the nature and objectives of the invention, reference should be made to the following detailed description, taken in connection with the accompanying drawings.

DETAILED DESCRIPTION

Figure 1:
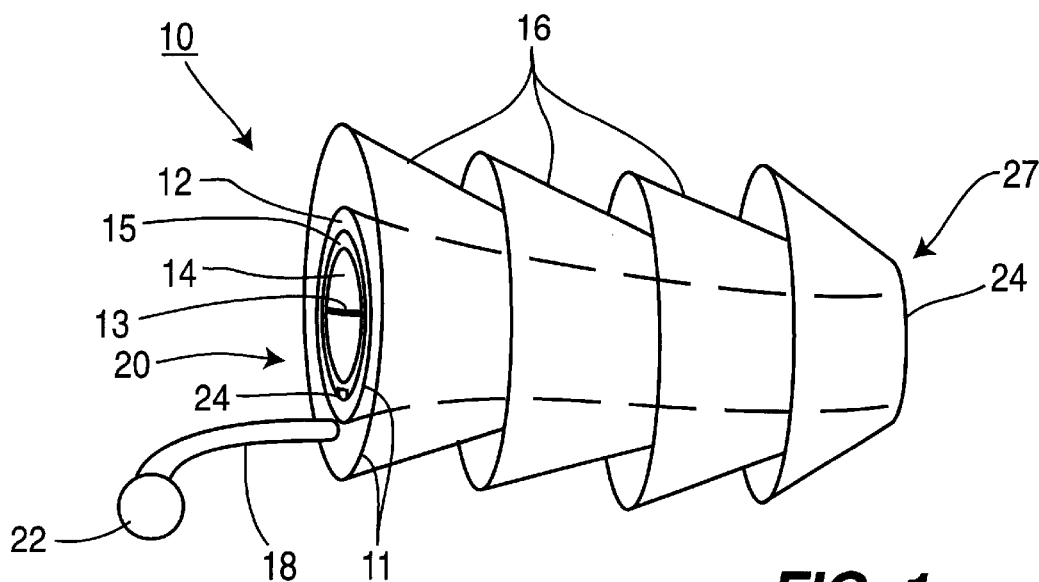
FIG. 1 is a perspective view of an earmold and casing of a first embodiment of the present invention.

Referring to FIG. 1, the hearing aid earmold and casing of a first embodiment of the present invention is generally designated as 10. An earmold 11 comprises a cylindrical tube 12 of a soft pliable material having a cylindrical passage 14 therethrough. A plurality of conical fins 16 project radially outwardly from the tube 12 and extend along the entire length of the tube 12. An integral pull 18 extends from a proximal end 20 of the tube 12. The pull 18 has a knob 22 on its end. A canal 24 is in the surface of the cylindrical passage 14 and extends the full length of the tube 12.

The earmold 11 is molded from an elastomer to assure to assure softness, durability and ease of use. Although various materials may be used to make the earmold 11, a preferred material is a heat cured silicone, which has an ideal combination of softness, durability, stability and demonstrated biocompatibility. Thermoplastic elastomers have the processibility of thermoplastics and the performance properties of thermoset rubber. Also, thermoplastic elastomers cost one-tenth to one-twentieth the cost of silicone materials. Another advantage of thermoplastic elastomers is their appearance and feel. Most are available in opaque, translucent or colorable grades and possess a smooth, warm feel.

In the use of the earmold 11, the entire electronics of the hearing aid may be inserted in the cylindrical passage 14. The electronics, including a microphone, receiver, battery and amplifier integrated circuit, may be mounted on a flexible printed circuit board 13 which is inserted in a hollow, flexible casing 15. The casing 15 can be of the same material of earmold 11 and is inserted into the passage 14 of earmold 11. Casing 15 may be slightly larger in diameter than the passage 14 so as to have a tight fit therein. Also, casing 15 could have a detent fitting in a recess in the wall of the passage 14 so as to secure casing 15 in the earmold 11. Alternatively, the electronics could be outside the earmold and connected to the earmold by a tube, such as shown in U.S. Pat. No. 5,002,151 to Oliveira et al.

The earmold 11, being very compliant, conforms to the general shape of casing 15 containing the electronics assembly. It is generally known that the ear canal has two natural bends therein, which are often referred to as the first and second bends. If the electronics assembly and casing are designed to have these bends as part of their form, and the earmold conforms to these bends, then the earmold takes on these natural bends which provides for mechanical locking. As the earmold and electronics assembly are pushed into the ear, the conical fins 16 compress as does the skin of the ear canal. Once the earmold is fully inserted, it has a soft but definite locking effect. The skin of the ear canal is then in its normal or uncompressed state, but the conical fins 16 of the remain compressed to some degree to hold the earnold firmly in the ear.

To use the hearing aid earmold and casing 10, the user inserts the earmold 11 into the ear with a distal end 27 of the tube 12 being inserted first. The user presses on the proximal end 20 of the tube 12 to push it into the ear. As the earmold 11 moves into the ear, the fins 16 gently compress as they travel inwardly. When the earmold 11 reaches the inner canal bend, the earmold 11 tends to lock into place. Thus, the earmold 11 is held in the ear of the user both mechanically and by friction. To remove the hearing aid earmold and casing 10, the user merely pulls on the pull 18 which is integrally molded on the proximal end 20 of the earmold 11. Thus, the hearing aid earmold and casing 10 can be easily inserted and removed from the ear. Since the earmold 11 is made of a soft, pliable material, it fits comfortably in the ear.

Venting is a means in earmolds to provide intentional sound leakage and to relieve a feeling of pressure in the ear. The canal 24 in the tube 12 provides for such a leakage. The canal 24 can be small, having a diameter of about 0.6 mm, so that it makes little difference to the frequency response and does not contribute to feedback. The canal 24, however, is effective in allowing pressure equalization to reduce the feeling of pressure that many hearing aid users experience. The canal 24 may be enlarged to effect frequency response and further improve the overall acoustic benefit provided the user.

Thus, there is provided by the present invention a hearing aid earmold and casing which is made of a soft, pliable molded material wherein the earmold has conical fins projecting from its outer surface. This provides an earmold which fits comfortably in the ear and is held in the ear both by friction and mechanically. The earmold can be made in a minimum of different sizes to fit a large variety of ear canal sizes. Since the earmold is of a pliable material and has the fins projecting therefrom, one size of earmold can fit into a large variety of ear canals. The earmold and casing can contain the entire electronics of the hearing aid, or the earmold can be connected to the electronics which is outside of the earmold by a connecting casing. In addition, the earmold and casing can be molded easily and inexpensively so that they are disposable.

Figure 2:
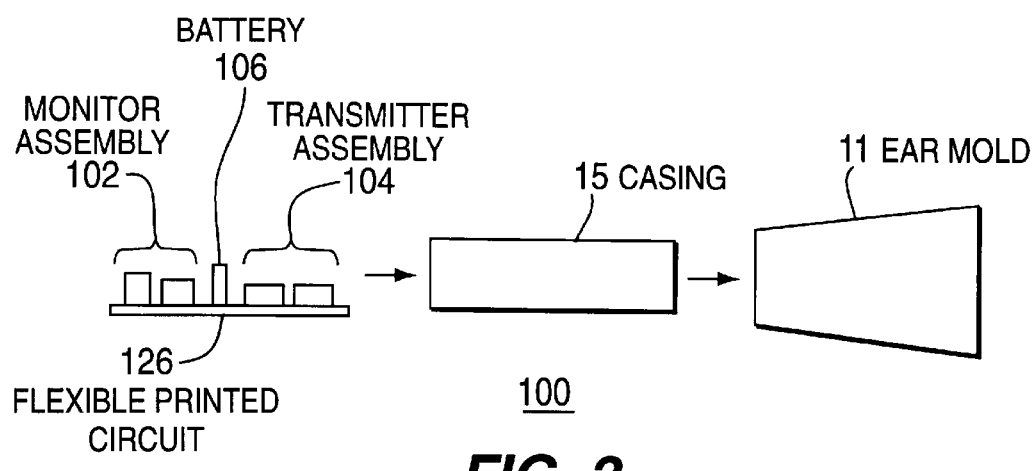
FIG. 2 is an exploded schematic view of a disposable in-the-ear monitoring instrument which is another embodiment of the present invention.
Figure 3:
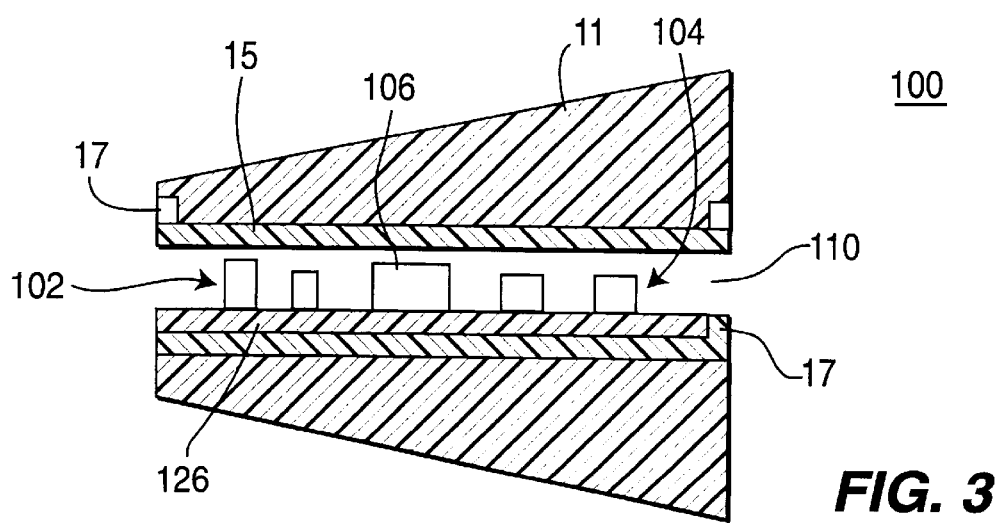
FIG. 3 is a cross-sectional view of the assembled disposable in-the-ear monitoring instrument.
Figure 4:
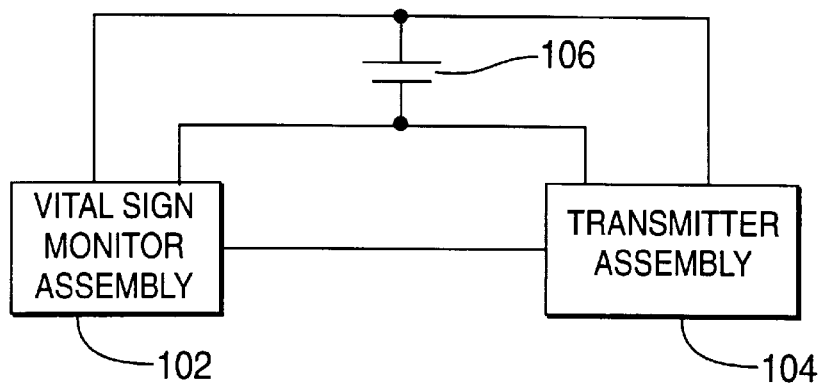
FIG. 4 is a schematic view of the monitor assembly, transmitter assembly and battery of the disposable in-the-ear monitoring instrument.
Figure 5:
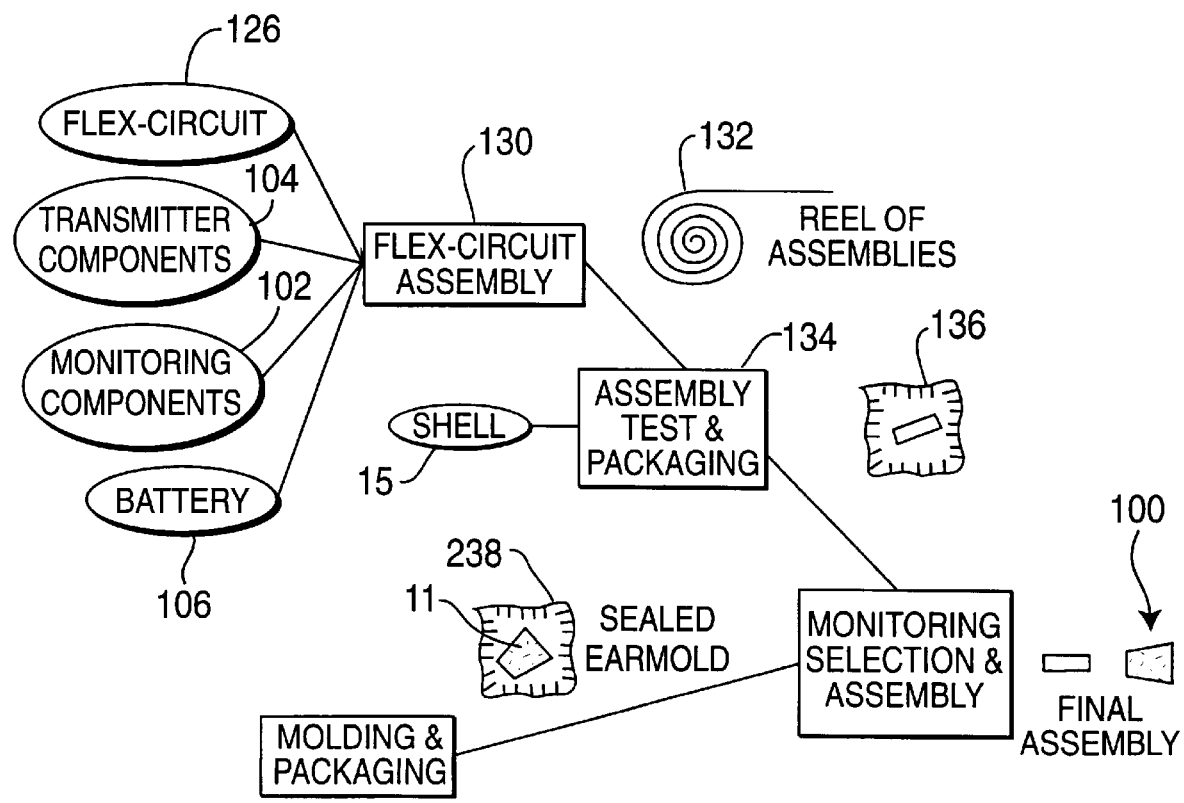
FIG. 5 is a flow chart showing a method of assembling the disposable in-the-ear monitoring instrument.

FIGS. 2–4 illustrate a disposable in-the-ear monitoring instrument 100, which is a second embodiment of the present invention. FIG. 5 shows the assembly of monitoring instrument 100. FIG. 2 shows the disposable in-the-ear monitoring instrument 100 as separated component elements, and FIG. 3 shows the disposable in-the-ear monitoring instrument 100 as assembled. With respect to FIGS. 2–5, like numerals indicate like elements relative to the hearing aid earmold and casing 10 of FIG. 1.

The disposable in-the-ear monitoring instrument 100 includes a monitoring assembly 102, a transmitter assembly 104, and a battery 106 disposed on a flexible printed circuit board 126. The flexible printed circuit 126 with the permanently mounted monitoring assembly 102, transmitter assembly 104, and battery 106 is positioned within casing 15. And casing 15 is in-turn positioned within earmold 11.

The monitoring assembly 102 includes miniaturized component elements for monitoring one or more vital health signs of the individual using the disposable in-the-ear monitoring instrument 100. The components of monitoring assembly 102 are conventional components used for measuring such vital health signs as pulse, temperature, heart rate, respiration or blood oxygenation, for example. Thus monitoring assembly 102 may comprise sufficient components to monitor one vital health sign of the user, or a plurality of vital health signs. Such components could, for example, include transducers such as a miniaturized microphone (not shown) monitoring heart rate and respiration by conveying pulse sounds and respiration sounds from the ear canal to an external monitor, to aid in the auscultation of a patient; a thermistor (not shown), thermocouple (not shown) or other heat sensitive transducer (not shown) to measure the temperature in the ear canal; and one or more light sources (not shown) and one or more photo-active devices (e.g. photocells, phototransistors) (not shown) to determine blood oxygenation by monitoring the color of light that is reflected from the blood vessels in the eardrum.

Although the description above only describes a single type of monitoring transducer in each instrument, it is contemplated that multiple components may be combined. For example, an instrument may include a thermistor and a microphone, a microphone and a photocell or all three types of devices. Furthermore, it is contemplated that one transducer may be used to measure multiple vital health signs. For example, a microphone may be used to measure both pulse and respiration rates and the light source and photocell may be used to measure both pulse rate and blood oxygenation. It is known that composite acoustical signals derived through a microphone, as described above, can be analyzed into their original and independent sources based, for example, on their relative timing, frequency spectra, or average energy levels.

Transmitting assembly 104 is electrically connected to monitoring assembly 102 and receives electrical signals representative of the one or more vital health signs being monitored. Transmitting assembly 104 transmits these signals to a receiving unit or station (not shown) which may further process the signals and from which medical personnel can observe, and if necessary record the monitored vital health signs of the user. It is contemplated that the transmitting assembly may include digitizing circuitry which converts the analog signals to digital form prior to transmission or it may transmit the analog signals directly.

The receiving unit may include, for example, band pass filters which separate portions of a signal received from a microphone in the monitoring instrument into a pulse rate signal and a respiration signal. At the same time, these filters may attenuate ambient noise and other sounds from the person being monitored. The receiving unit may also include processing circuitry which analyzes color signals returned by photocell or photocells in the monitoring instrument to calculate blood oxygenation.

Sound signals provided by the monitoring unit to the receiving unit may be analyzed into component sounds to monitor normal vital health signs, in which case, an alarm condition may occur when the normal vital health signs are interrupted. Alternatively, the sound signals may be analyzed for abnormal conditions, such as fibrillation, arterial gallop, ventricular gallop, labored or rapid respiration or other abnormal sounds emitting from the heart or lungs, and an alarm condition may occur only when one of these abnormal sounds is detected.

Transmitter assembly 104 may comprise the components of any conventional transmitter such as an infrared transmitter, a radio wave transmitter, microwave transceiver, or any combination of the foregoing. One type of microwave transceiver that can be used in monitoring instrument 100 conveys data by modulating the impedance of a microwave antenna. An exemplary transceiver of this type is disclosed in U.S. Pat. No. 5,491,482, entitled ELECTRONIC SYSTEM AND METHOD FOR REMOTE IDENTIFICATION OF CODED ARTICLES AND THE LIKE, which is incorporated herein by reference for its teaching on microwave transceivers. In the instance where the transmitter assembly 104 is a microwave transceiver, the remote monitoring unit may include an interrogator/reader unit which is capable of interrogating the microwave transceiver and which thereby can identify one individual using a particular disposable in-the-ear monitoring instrument 100 from among a plurality of individuals each of whom is using a disposable monitoring instrument. Alternatively, the transmitting assembly 104 may comprise an infrared diode which is modulated to transmit data from the monitoring instrument to the receiving unit as an infrared beam. For this type of transmitting assembly to operate most effectively, it is desirable for the infrared diode to be positioned in the opening of the ear canal in the concha. The transmitting assembly 104 may, alternatively, include a tunnel diode radio-frequency transmitter. To conserve power in any of these transmitter assemblies 104, it is contemplated that timing circuitry in the instrument 100 may periodically activate and then deactivate the transmitter assembly.

A suitable battery 106 is also disposed on or connected to the flexible printed circuit 26 and is connected to and thereby operates transmitter assembly 104. If necessary, battery 106 may also be connected to monitoring assembly 102 to operate any components of the monitoring assembly 102. FIG. 4 schematically shows battery 106 electrically connected to transmitter 104 and monitoring assembly 102. The particular battery 106 used depends on the desired operating life and the preferred operating voltage of the disposable in-the-ear monitoring instrument 100. Typically, a battery-life of 5 days is desired for monitoring instrument 100. Nonetheless extended battery life can result by utilizing more efficient components comprising the transmitter assembly 104 and monitoring assembly 102.

As shown in FIG. 3, the printed circuit 126, with monitoring assembly 102, transmitter assembly 104, and battery 106 permanently mounted thereon, is housed within and protected by the casing 15 which, as previously noted, is a flexible hollow cylindrical element. Typically, casing 15 includes means such as ribs 17 to orient and retain printed circuit 126 and the monitoring and transmitter assemblies mounted thereon.

Alternatively, the printed circuit 126 may be coated with a potting compound, such as epoxy and the battery may be formed above and/or around the printed circuit 126 to fill the casing 15. Casing 15 includes means, such as ribs 19, which mate with earmold 11 so that casing 15 is retained permanently within earmold 11. The outer configuration of earmold 11 includes ribs 16 which are generally conical in-shape, and of an appropriate size and configuration to comfortably fit within the ear canal of the user. Because earmold 11 is ribbed and of a soft, durable and compliant material, it flexibly molds itself to the shape of the user's ear canal. Typically, only one size earmold 11 fits most adults. Because the earmold 11 conforms to a wide variety of ear shapes, however, even if one size of earmold does not fit all users, a relatively small number of differently-sized earmolds may be made to cover essentially all users. Because the earmold 11 is of a compliant material, it provides a good fit within the user's ear canal and is comfortable. These properties assist the monitoring assembly 102 in providing accurate readings of the monitored vital health signs as the user is less likely to interfere with the instrument by attempting to reposition it.

It is desirable for the monitoring instrument to not interfere with the user's hearing when it is in place. This may be done by including a receiver and hearing-aid circuitry on the monitoring instrument or by allowing for the passage of sounds through the monitoring instrument. The exemplary embodiment of the invention shown in FIG. 3 uses the second method. Extending longitudinally through the disposable in-the-ear monitoring instrument 100 is a relatively unobstructed passage 110 approximately 2 millimeters in diameter. Passage 110 provides venting when monitoring instrument 100 is disposed in the user's ear and also provides a means by which outside sounds may enter the ear canal. Although the passage 110 is shown as being partially obstructed by electrical components of the monitoring circuitry, it is contemplated that the monitoring circuitry, including the battery, may be formed as a cylinder (not shown) which is sealed in the casing 15 such that an unobstructed passageway 110 exists in the casing 15 and in the assembled monitoring instrument. Thus, monitoring instrument 100 should not significantly affect the user's ability to hear. If, instead, a conventional hearing aid is incorporated in the disposable in-the-ear monitoring instrument 100, the hearing aid may include, for example, a unity gain amplifier or may include an amplifier which compensates for a known hearing loss of the person being monitored.

Referring to FIG. 5, a method is shown of assembling the disposable in-the-ear monitoring instrument 100 of the present invention. A flexible printed circuit 126 is fed from a reel to a flexible circuit assembly apparatus 130. Also fed to the flexible circuit assembly apparatus 130 are transmitter components comprising transmitter assemblies 104, and monitoring components which include monitoring assemblies 102, as well as batteries 106. At the flexible circuit assembly apparatus 130, the components and batteries are assembled onto the flexible printed circuit 126 to form a strip containing a plurality of individual assemblies intended for the manufacture of a plurality of disposable in-the-ear monitoring instruments 100. If the assemblies are encased, they may be coated with a flexible potting compound and the battery components may be formed except for the electrolyte. The completed assemblies are mounted on a reel of assemblies 132.

The assemblies comprising reel 132 are then fed along with casings 15 into an assembler 134 where each individual assembly is cut apart from the reel 132, and is installed in a casing 15. Optionally, if the assemblies are encased in the potting compound and the battery electrodes formed on the encased assemblies, the battery electrolyte may be added to the casing and the casing may be sealed to form the completed battery. The casing assembly is then inserted into a package 136 which is hermetically sealed and contains a gas which protects the casing assembly from the atmosphere, and also suspends battery activity. Thus, at this point in the assembly of the disposable in-the-ear monitoring instrument, each casing 15 contains components capable of monitoring one or a plurality of pre-selected vital health signs and a miniaturized transmitter capable of transmitting signals representing the monitored vital health signs to a remote monitoring unit.

In a separate manufacturing step, earmolds 11 are molded and packaged in a hermetically sealed package 138. Earmolds 11 are typically molded in one size suitable to accommodate most adult users.

In the last step of the assembly process, a physician or other medical personnel determines the vital health signs which are to be monitored and thereby selects a casing 15 containing a monitoring assembly capable of determining such vital health signs and an earmold 11 appropriate for the patient being monitored and places that casing 15 into the earmold 11. Thus for example if only the user's pulse is to be monitored, a casing 15 containing a pulse monitoring assembly would be selected, but if, for example, the user's pulse, respiration and blood oxygenation are to be monitored, another casing 15 containing an appropriate monitoring assembly would be selected.

The disposable in-the-ear monitoring instrument 100 is used only for the life of the battery permanently housed therein. Accordingly, there is no need for an on/off switch, especially if a metal-air type battery, such as a zinc-air battery, is used. Removing the monitor from the sealed package would activate the battery and the devices would continue to operate until the battery is depleted. The overall design of the monitoring assembly 102 and transmitter assembly 104 are purposely kept relatively simple using a minimum number of components to accommodate automated assembly. Thus, the monitoring assembly 102 and transmitter assembly 104 are inexpensive because they can be manufactured in large volumes resulting in an economy of scale. In addition, the monitoring assembly 102 and transmitter assembly 104 are easily encased in the simple hollow casing 15. Furthermore, earmold 11 is of a simple design and of a soft, pliable material so that it too is inexpensive.

The resulting disposable in-the-ear monitoring instrument 100 is of a minimum number of inexpensive parts, easily assembled, easy to use and relatively inexpensive compared with presently used monitoring instruments, which are much more complex and cumbersome to use. A clear advantage, therefore, of the present invention is its disposability. That is, once the battery in the monitoring instrument 100 has expired, the unit is disposed and replaced with a new monitoring instrument 100. The disposability of the monitoring instrument is also advantageous for minimizing the spread of disease.

Although the disposable in-the-ear monitoring instrument 100 is inexpensive and simpler to use than conventional monitoring instruments, it is nonetheless highly reliable. In addition to its disposability and relatively low cost, the monitoring instrument 100 of the present invention is also more comfortable for the user than other presently used monitoring instruments.

Although the present invention has been described in relation to particular embodiments thereof, many other variations and modifications will become apparent to those skilled in the art. It is preferred, therefore, the present invention be limited not by the specific disclosure herein, but only by the appended claims.

What is claimed:

1. A disposable in-the-ear monitoring instrument, comprising:
   one or more transducers for monitoring vital health signs of a user,
   a transmitter for receiving signals from said one or more transducers representative of monitored vital health signs and for transmitting said signals to a remote location,
   a battery electrically connected to the transmitter,
   a flexible casing for housing said one or more transducer, said transmitter and said battery, and
   an earmold of a soft, pliable material and having a plurality of fins projecting outwardly, said earmold for housing said casing with said one or more transducers, said transmitter and said battery.

2. The disposable in-the-ear monitoring instrument according to claim 1, wherein the earmold and casing are each tube like in shape, said earmold having an inside diameter which is expandable to receive said casing, and said casing is fully enclosed within said earmold.

3. The disposable in-the-ear monitoring instrument according to claim 1, wherein said one or more transducers, said transmitter and said battery are electrically connected to a flexible circuit board and are housed in said casing.

4. The disposable in-the-ear monitoring instrument according to claim 1, wherein the fins are along the entire length of the earmold.

5. The disposable in-the-ear monitoring instrument according to claim 4, in which the fins are conical.

6. The disposable in-the-ear monitoring instrument according to claim 4, in which said earmold is cylindrical and has a cylindrical passage therethrough, the cylindrical passage defining an inside surface of said earmold.

7. The disposable in-the-ear monitoring instrument according to claim 6, in which said earmold has first and second ends and said cylindrical passage extends from said first end to said second end and the casing includes a cylindrical passage which extends from said first end to said second end, wherein when said casing is inserted into said earmold, said cylindrical passage in the casing forms a passageway through which air and sounds may pass between first and second ends of said earmold casing.

8. The disposable in-the-ear monitoring instrument according to claim 7, wherein the cylindrical passage in the casing has a diameter of approximately 2 millimeters.

9. The disposable in-the-ear monitoring instrument according to claim 7, in which said earmold is made of a thermoplastic elastomer.

10. The disposable in-the-ear monitoring instrument according to claim 1, wherein said one or more transducers include a pulse monitor comprising a microphone and an amplifier, the microphone being positioned in the monitoring instrument to be proximate to the user's ear.

11. The disposable in-the-ear monitoring instrument according to claim 1, wherein said one or more transducers include at least one light source and at least one photo-active element, the light source being positioned to illuminate the user's ear drum and the at least one photo-active element being positioned to measure changes in color of light reflected from blood vessels in the user's ear drum to collect data relevant to blood oxygenation.

12. The disposable in-the-ear monitoring instrument according to claim 1, wherein said one or more transducers include a heat sensitive transducer to measure the user's internal body temperature.

13. The disposable in-the-ear monitoring instrument according to claim 1, wherein said one or more transducers include a microphone for auscultating the user's pulse.

14. The disposable in-the-ear monitoring instrument according to claim 1, wherein said one or more transducers include a microphone for auscultating the user's respiration.

15. The disposable in-the-ear monitoring instrument according to claim 1, wherein said one or more transducers include a microphone for auscultating the user's lung sounds to detect abnormal respiratory sounds.

16. The disposable in-the-ear monitoring instrument according to claim 1, wherein said one or more transducers include a microphone for auscultating the user's heart to detect fibrillation, arterial gallop, ventricular gallop or other abnormal sounds emitting from the heart.

17. The disposable in-the-ear monitoring instrument according to claim 1, wherein said transmitter is a radio frequency transmitter.

18. The disposable in-the-ear monitoring instrument according to claim 1, wherein said transmitter is an infrared transmitter.

19. The disposable in-the-ear monitoring instrument according to claim 1, wherein said transmitter is a microwave transceiver.

20. The disposable in-the-ear monitoring instrument according to claim 11, wherein said casing includes means to orient and retain the one or more transducers and the transmitter.

21. The disposable in-the-ear monitoring instrument according to claim 1, wherein said battery is electrically connected to said one or more transducers.

22. The disposable in-the-ear monitoring instrument according to claim 1, further comprising a hearing aid.

23. The disposable in-the-ear monitoring instrument according to claim 20, wherein said hearing aid includes a unity gain amplifier.

24. A method of making a disposable in-the-ear monitoring instrument, comprising the steps of:
  mounting electrical components, monitoring components and batteries onto an elongated flexible printed circuit strip to form there along the assembly of a plurality of disposable in-the-ear monitoring instruments;
  cutting the flexible printed circuit strip apart to form individual assemblies of one or more of the monitoring components, a transmitter and a battery of a disposable in-the-ear monitoring instrument on a printed circuit;
  inserting each assembly into a separate flexible casing; and
  inserting a flexible casing containing an assembly into an opening in an earmold formed from a soft, durable and complaint material and having an outer surface, said earmold having a plurality of fins extending from said outer surface.

25. The method according to claim 24, wherein after said electrical components, monitoring components and batteries are mounted on said flexible printed circuit strip, said strip is mounted on a reel.

26. The method according to claim 25, wherein said flexible printed circuit strip on said reel is fed, with casings, into an assembler which cuts the strip apart into said individual assemblies and inserts each assembly into a separate casing.

27. The method according to claim 26, wherein the battery is a zinc-air battery and, after said assemblies are inserted into said casings, said casings containing said assemblies are disposed into a package which is hermetically sealed and which contains a gas, whereby the casing and assembly are protected from atmospheric contamination and any electrical activity in the battery is significantly reduced.

28. The method according to claim 27, wherein said earmolds are molded and packaged in an hermetically sealed package.

29. The method according to claim 28, wherein a suitable earmold and casing suitable for monitoring one or more vital health signs are removed from their individual packages and assembled to form a disposable in-the-ear monitoring instrument.

30. The method according to claim 24, wherein said monitoring components are assembled onto said elongated flexible printed circuit strip to form individual monitoring assemblies capable of monitoring, for a particular user, one or a plurality of vital health signs of the user.

31. The method according to claim 30, wherein said earmolds are made in a predetermined number of different sizes, and a casing suitable for the particular monitoring needs of the user is inserted into an earmold of an appropriate size for the user.

32. The method according to claim 24, wherein said casing and earmold are each generally cylindrical in shape, and said earmold has an inside diameter which is expandable to receive said casing, and said casing is fully enclosed within said earmold.

* * * * *